ably Industries
United States Patent [19]

Sekiya et al.

[11] Patent Number: 4,668,682
[45] Date of Patent: May 26, 1987

[54] 2-PHENYLALKYL-3-AMINOALKYL-4(3H)-QUINAZOLINONE COMPOUND

[75] Inventors: Tetsuo Sekiya; Mikio Tsutsui; Daijiro Horii; Akira Ishibashi, all of Ami, Japan

[73] Assignee: Mitsubishi Chemical Industries Limited, Tokyo, Japan

[21] Appl. No.: 753,708

[22] Filed: Jul. 10, 1985

[30] Foreign Application Priority Data

Jul. 26, 1984 [JP] Japan .................. 59-154086

[51] Int. Cl.[4] .................. A61K 31/505; C07D 239/91; C07D 401/06
[52] U.S. Cl. .................. 514/259; 514/212; 514/234; 540/600; 544/119; 544/287
[58] Field of Search .............. 544/287, 119; 514/259, 514/234, 212; 260/243.3

[56] References Cited

U.S. PATENT DOCUMENTS 3,748,327  7/1973  Beyerle et al. .................. 544/287

OTHER PUBLICATIONS

Boltze et al., "Chemical Abstracts", vol. 63, 1965, col. 4289d.
Dash et al., "Chemical Abstracts", vol. 94, 1981, col. 94:47259x.

Primary Examiner—Richard L. Raymond
Assistant Examiner—James H. Turnipseed
Attorney, Agent, or Firm—Frishauf, Holtz, Goodman & Woodward

[57] ABSTRACT

Disclosed are a 2-phenylalkyl-3-aminoalkyl-4(3H)-quinazolinone compound of Formula (1):

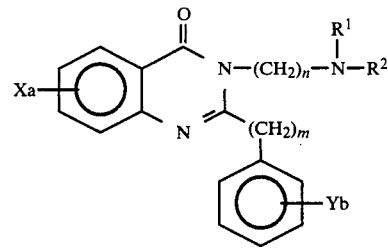

wherein, X represents a hydrogen atom, an alkyl group having 1 to 5 carbon atoms, an alkoxy group having 1 to 5 carbon atoms, a phenoxy group, a benzyloxy group, a halogen atom or a hydroxy group; Y represents an alkyl group having 1 to 5 carbon atoms, an alkoxy group having 1 to 5 carbon atoms, a benzyloxy group, a halogen atom or a nitro group; $R^1$ represents a hydrogen atom or an alkyl group having 1 to 5 carbon atoms; $R^2$ represents an alkyl group having 1 to 5 carbon atoms or a group of Formula (2)

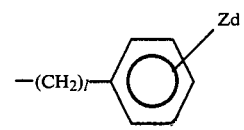

[wherein, Z represents a hydrogen atom, an alkyl group having 1 to 5 carbon atoms, an alkoxy group having 1 to 5 carbon atoms or a halogen atom; d is an integer of 1 to 3; and l is an integer of 1 to 5]; or $R^1$ and $R^2$ represent together with the nitrogen atom to which they are attached, a cyclic amino group of the formula:

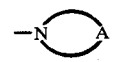

[wherein, A represents an alkylene group having 2 to 6 carbon atoms or a group of the formula —(CH$_2$)$_2$—O—(CH$_2$)$_2$—]; a and b are independently an integer of 1 to 3; and n and m are independently an integer of 1 to 5, or a pharmaceutically acceptable acid addition salt thereof, a process for preparing said compound, a composition comprising said compound as an active ingredient and a method of treatment by use of said compound.

The compounds of the present invention have calcium antagonistic, vasodilative, and antihypertensive activities.

19 Claims, No Drawings

2-PHENYLALKYL-3-AMINOALKYL-4(3H)-QUINAZOLINONE COMPOUND

BACKGROUND OF THE INVENTION

This invention ralates to a novel 4(3H)-quinazolinone compound, and more particularly, a 2-phenylalkyl-3-aminoalkyl-4(3H)-quinazolinone compound having calcium antagonistic, vasodilative, and antihypertensive activities, or a parmaceutically acceptable acid addition salt thereof, to a process for preparing said compound, to a composition having calcium antagonistic activity and comprising said compound as an active ingredient, and to a method of dilating blood vessels or reducing the level of blood pressure based on calcium antagonistic activity.

With respect to a 2-phenylalkyl-3-aminoalkyl-4(3H)-quinazolinone derivative, there has been reported that 2-phenylmethyl-3-(2-diethylaminoethyl)-4(3H)-quinazolinone of the formula:

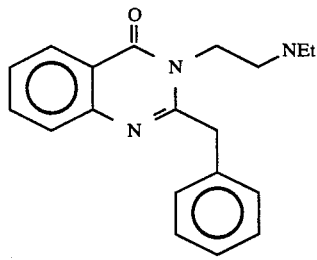

has an antispasmodic activity [Arzneim. Forch. 13, 688 (1963)].

Moreover, although there has been known 2-phenylmethyl-3-(2-aminoethyl)-4(3H)-quinazolinone of the formula:

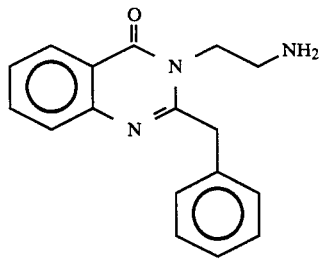

any pharmacological activity thereof has not been reported [J. Indian Chem. Soc., 57, 835 (1980)].

Further, in U.S. Pat. No. 3,558,610, there has been described that a 4(3H)-quinazolinone derivative of the general formula:

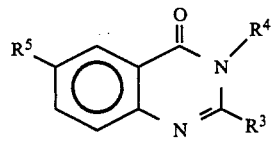

wherein, $R^3$ represents a phenyl alkyl group, etc.; $R^4$ represents a di-lower alkylamino group, etc.; $R^5$ represents an amino group, an alkanoylamino group, a benzylideneamino group or a nitrofurylideneamino group, is useful as an anti-inflammatory or antimicrobial agent. However, of the compounds described in the Examples of the above Patent, compounds in which $R^3$ is a phenylalkyl group, or $R^4$ is a di-lower alkylamino group are only two compounds of the following formulas:

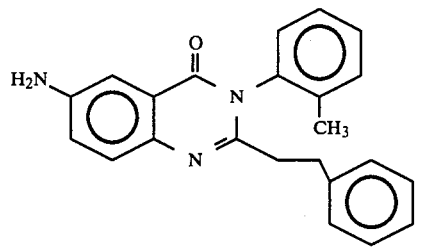

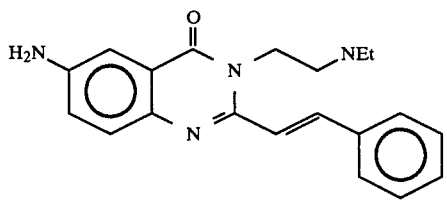

and there have been described no compounds in which $R_3$ is a phenylalkyl group and simultaneously $R^4$ is a di-lower alkylamino group. The compounds disclosed therein are ones in which $R^5$ is always an amino group or a substituted amino group and are different from the compounds of the present invention.

Still further, there has been reported that 2-methyl-3-(3-dibutylaminopropyl)-6-chloro-4(3H)-quinazolinone of the following formula:

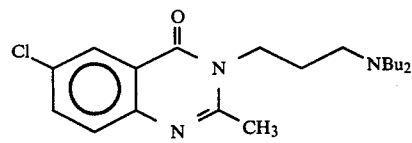

has the inhibitive activity of acetylcolinesterase, although it is not a 2-phenylalkyl-3-aminoalkyl-4(3H)-quinazolinone derivative [Indian J. Pharm., 33, 80 (1971)].

THE SUMMARY OF THE INVENTION

An object of the present invention is to provide a novel and useful 2-phenylalkyl-3-aminoalkyl-4(3H)-quinazolinone derivative.

Based on the knowledge described above, the present inventors have made intensive studies, and as a result, have accomplished the present invention. Namely, the novel and useful 2-phenylalkyl-3-aminoalkyl-4(3H)-quinazolinone derivative of the present invention is a compound of Formula (1):

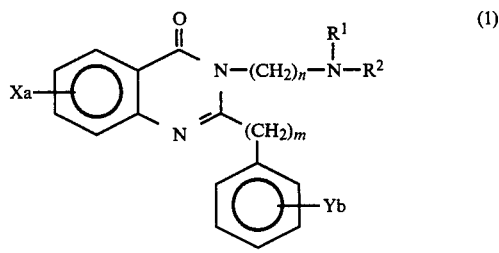

wherein, X represents a hydrogen atom, an alkyl group having 1 to 5 carbon atoms, an alkoxy group having 1 to 5 carbon atoms, a phenoxy group, a benzyloxy group, a halogen atom or a hydroxy group; Y represents an alkyl group having 1 to 5 carbon atoms, an alkoxy group having 1 to 5 carbon atoms, a benzyloxy group, a halogen atom or a nitro group; $R^1$ represents a hydrogen atom or an alkyl group having 1 to 5 carbon atoms; $R^2$ represents an alkyl group having 1 to 5 carbon atoms or a group of Formula (2)

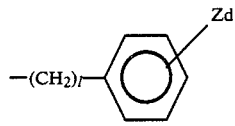

[wherein, Z represents a hydrogen atom, an alkyl group having 1 to 5 carbon atoms, an alkoxy group having 1 to 5 carbon atoms or a halogen atom; d is an integer of 1 to 3; and l is an integer of 1 to 5]; or $R^1$ and $R^2$ represent together with the nitrogen atom to which they are attached, a cyclic amino group of the formula:

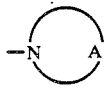

[wherein, A represents an alkylene group having 2 to 6 carbon atoms or a group of the formula —(CH$_2$)$_2$—O—(CH$_2$)$_2$—]; a and b are independently an integer of 1 to 3; and n and m are independently an integer of 1 to 5, or a pharmaceutically acceptable acid addition salt thereof.

DESCRIPTION OF THE PREFERRED EMBODIMENTS

In above Formula (1), the alkyl group having 1 to 5 carbon atoms represented by X or Y includes, for example, a methyl group, an ethyl group, an n-propyl group, an isopropyl group, an n-butyl group, a sec-butyl group, and a pentyl group; the alkoxy group having 1 to 5 carbon atoms represented by X or Y includes, for example, a methoxy group, an ethoxy group, an n-propoxy group, an isopropoxy group, an n-butoxy group, a sec-butoxy group, an n-pentoxy group and an isopentoxy group; and the halogen atom represented by X or Y includes a fluorine atom, a chlorine atom, a bromine atom and an iodine atom.

The alkyl group having 1 to 5 carbon atoms of $R^1$ or $R^2$ includes, for example, a methyl group, an ethyl group, an n-propyl group, an isopropyl group, an n-butyl group, a sec-butyl group and a pentyl group. In cases where $R_2$ is an aralkyl group represented by Formula (2), the alkyl group having 1 to 5 carbon atoms represented by Z includes, for example, a methyl group, an ethyl group, an n-propyl group, an isopropyl group, an n-butyl group, a sec-butyl group and a pentyl group; the alkoxy group having 1 to 5 carbon atoms represented by Z includes, for example, a methoxy group, an ethoxy group, an n-propoxy group, an isopropoxy group, an n-butoxy group, a sec-butoxy group and an n-pentoxy group; and the halogen atom represented by Z includes a fluorine atom, a chlorine atom, a bromine atom and an iodine atom. The cyclic amino group of the formula:

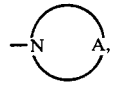

which is formed by $R^1$ and $R^2$ together with the nitrogen atom to which they are attached, includes, for example, an azilidino group, a pyrrolidino group, a pyperidino group, a hexamethyleneimino group and a morpholino group. X, Y and Z each may be mono-substituted, di-substituted or tri-substituted. In cases where X is di-substituted or tri-substituted, the substituents thereof may be the same or different. In cases where Y is di-substituted or tri-substituted, the substituents thereof may be the same or different. In cases where Z is di-substituted or tri-substituted, the substituents thereof may be the same or different.

The term "pharmaceutically acceptable acid addition salt" used herein means an addition salt of an acid which does not increase substantially toxicity of the basic compound.

These acid addition salts include, for example, a salt with an mineral acid such as hydrochloric acid, sulfuric acid and phosphoric acid, and with an organic acid such as acetic acid, malonic acid, fumaric acid, maleic acid, succinic acid, tartaric acid, methanesulfonic acid, paratoluenesulfonic acid and glucuronic acid. Such an acid addition salt can be obtained by dissolving the compound of the present invention in a suitable solvent and then adding thereto an acid as such or after dissolved in a suitable solvent. The suitable solvent includes, for example, ether and ethanol.

The compounds of the present invention have a pharmacological activity such as calcium antagonistic activity, vasodilative activity, antihypertensive activity and the like, and are useful as medical preparations for a cardiopathy and a circulatory disease. Moreover, these compounds are also useful as active ingredients for pharmaceutical preparations having activities of dilating blood vessels and enhancing effects of carcinostatics based on the calcium antagonistic activity.

The compound of the present invention may be administered orally or parenterally to a human being in an ordinary manner. When orally administered, it is preferable to administer the compound in an amount of 1 to 100 mg per one dosage, 1 to 3 times a day; when administered by intravenous injection, it is preferable to administer the compound in an amount of 0.01 to 10 mg l per one dosage, 1 to 5 times a day; and when administered through intestinum rectum, it is preferable to administer the compound in an amount of 1 to 100 mg per one dosage, 1 to 3 times a day. Compound (1) of the present invention or a salt thereof is generally administered in a form of a composition containing a carrier, a vehicle and the other additives usually employed for medical preparations. The medical carrier may be either solid or liquid and the solid carrier includes, for example, lactose, kaoline, starch, crystalline cellulose, corn starch, talc, agar, pectin, acacia, stearic acid, magnesium stearate, lecthin, sodium chloride and the like. The liquid carrier includes, for example, syrup, glycerin, peanut oil, polyvinylpyrrolidone, olive oil, ethanol, benzyl alcohol, propylene glycol, water and the like.

The medical preparations containing the compound of the present invention may take various forms. When the solid carrier is used, they may take a form of tablets; powders; granules; powders or granules encapsulated in a hard gelatin; suppositories or troches.

When the liquid carrier is used, the medical preparations may take a form of syrups; emulsions; soft gelatin capsules; sterilized injections, for example, sealed in an ampul, or aqueous or non-aqueous suspensions.

The compound of Formula (1) of the present invention may be also used as a cyclodextrin clathrate compound or through procedures of incorporating the compound of the present invention or the salt thereof in a ribosome.

Methods for preparing the compound of the present invention will be described below.

The compound of Formula (1) of the present invention can be prepared, for example, according to the following Synthesis processes A to E.

Synthesis process A

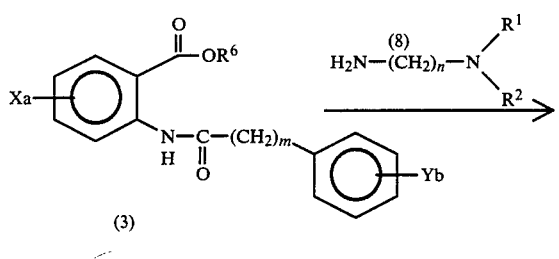

(3)

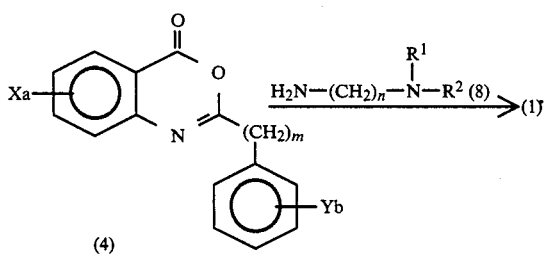

Synthesis process B

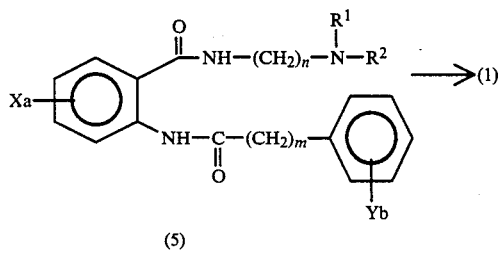

Synthesis process C

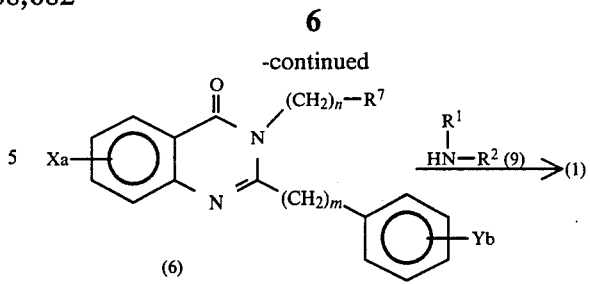

Synthesis process D

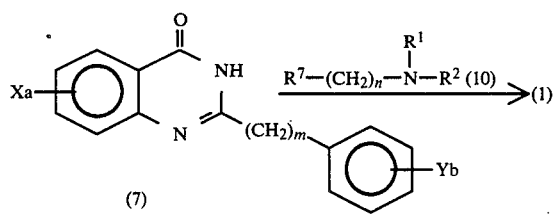

Synthesis process E

-continued wherein, X, Y, $R^1$, $R^2$, a, b, m and n have the same meanings as defined above; $R^6$ represents a hydrogen atom and an alkyl group having 1 to 5 carbon atoms; and $R^7$ represents a halogen atom or a mesyloxy or tosyloxy group.

Synthesis process A

Synthesis process A is a method for preparing the compound of Formula (1) in which an N-(phenylalkylcarbonyl) anthranilic acid or an ester thereof (3) and a diamine (8) are condensed to form a ring therebetween. The diamine (8) may be used in an amount of 0.5 to 5 equivalent ot he anthranilic acid or the ester thereof (3). The reaction solvent, although not restricted if its does not participate in the reaction, includes, for example, aromatic hydrocarbons such as benzene, toluene and xylene; ethers such as tetrahydrofuran, dioxane and ethylene glycol diethyl ether; ketones such as acetone and methyl ethyl ketone; ethyl acetate; dimethylformamide; dimethylacetamide; dimethyl sulfoxide and the like. The reaction temperature may be in the range of from 0° to 250° C. and preferably from 100° to 200° C. The reaction time may be in the range of from 30 minutes to 48 hours and preferably 1 to 24 hours. If desired, an acid or a base may be added to the reaction system as a catalyst.

Synthesis process B

Synthesis process B is a method for preparing the compound of Formula (1) in which a 2-phenylalkyl-4H-3,1-benzoxazine-4-one (4) and a diamine (8) are condensed to form a ring therebetween. The diamine (8) may be used in an amount of 0.5 to 5 equivalent to the 4H-3,1-benzoxazin-4-one (4). The reaction solvent, although not restricted if it does not participate in the reaction, includes, for example, aromatic hydrocarbons such as benzene, toluene and xylene; ethers such as tetrahydrofuran, dioxane and ethylene glycol diethyl ether; ketones such as acetone and methyl ethyl ketone; ethyl acetate; dimethylformamide; dimethylacetamide; dimethyl sulfoxide and the like. The reaction temperature may be in the range of from 0° to 250° C. and preferably from 50° to 150° C. The reaction time may be in the range of from 30 minutes to 48 hours and preferably 1 to 24 hours. If desired, an acid or a base may be added to the reaction system as a catalyst.

Synthesis process C

Synthesis process C is a method for preparing the compound of Formula (1) in which an N-substituted aminoalkyl-2-phenylalkylcarbonylaminobenzoic amide (5) is condensed to form a ring. The reaction may be carried out without any solvent or in an solvent which does not participate in the reaction, for example, aromatic hydrocarbons such as benzene, toluene and xylene; ethers such as tetrahydrofuran, dioxane and ethylene glycol diethyl ether; ketones such as acetone and methyl ethyl ketone; ethyl acetate; acetic anhydride; dimethylformamide; dimethylacetamide; dimethyl sulfoxide and the like. The reaction temperature may be in the range of from 0° to 250° C. and preferably from 100° to 150° C. The reaction time may be in the range of from 30 minutes to 48 hours and preferably 1 to 24 hours. If the case demands, an acid may be added to the reaction system as a catalyst.

Synthesis process D

Synthesis process D is a method for preparing the compound of Formula (1) in which a 2-phenylalkyl-3-(halogenoalkyl or sulfonyloxyalkyl)-4(3H)-quinazolinone derivative (6) and an amine (9) are subjected to raction with each other. The amine (9) may be used in an amount of 0.5 to 5 equivalent to the 4(3H)-quinanzolinone derivative (6). The reaction solvent, although not restricted if it is inert to the reaction, includes, for example, aromatic hydrocarbons such as benzene, toluene and xylene; alcohols such as methanol, ethanol and isoamyl alcohol; ethers such as tetrahydrofuran, dioxane and ethylene glycol diethyl ether; ketones such as acetone and methyl ethyl ketone; ethyl acetate; dimethylformamide; dimethylacetamide; dimethyl sulfoxide and the like. The reaction temperature may be in the range of from 0° to 250° C. and preferably from 50° to 150° C. The reaction time may be in the range of from 30 minutes to 48 hours and preferably 1 to 24 hours. When the reaction is carried out, an excess of the amine (9), for example, an organic amine such as triethylamine, pyridine, diazacycloundecene (DBU), or an inorganic base such as sodium hydroxide, potassium hydroxide, sodium carbonate, sodium hydrogencarbonate should preferably be present in the reaction system as an acid removing agent, for the smooth progress of the reaction.

Synthesis process E

Synthesis process E is a method for preparing the compound of Formula (1) in which a 2-phenylmethyl-4(3H)-quinazolinone (7) and an aminoalkyl halide (or an aminoalkyl sulfonate) (10) are subjected to raction with each other. The aminoalkyl halide (or the aminoalkyl sulfonate) (10) may be used in an amount of 0.5 to 5 equivalent to the 4(3H)-quinazolinone (7). The reaction solvent, although not restricted if it is inert to the reaction, includes, for example, aromatic hydrocarbons such as benzene, toluene and xylene; alcohols such as methanol, ethanol and isoamyl alcohol; ethers such as tetrahydrofuran, dioxane and ethylene glycol diethyl ether; ketones such as acetone and methyl ethyl ketone; ethyl acetate; dimethyl-formamide; dimethylacetamide; dimethyl sulfoxide and the like. The reaction temperature may be in the range of from 0° to 250° C. and preferably from 50° to 150° C. The reaction time may be in the range of from 30 minutes to 48 hours and preferably 1 to 24 hours. When the reaction is carried out in the presence of a base such as sodium metal, sodium hydride, potassium t-butoxide, the reaction proceeds smoothly.

Next, the present invention will be explained more specifically by the following Examples, by which however the present invention should not be limited.

EXAMPLE

Synthesis example 1

N-(2-Methoxyphenylacetyl)-anthranilic acid methyl ester

To a mixed solution of acetone (300 ml) and a 6% aqueous potassium carbonate solution (200 ml) there were added 10.2 g (67 mmol) of methyl ester of anthranilic acid. 12.5 g (67 mmol) of 2-Methoxyphenylacetic acid chloride were added dropwise under cooling thereto and the resulting reaction mixture was stirred at room temperature for 4 hours. The resulting precipitates were collected by filtration to obtain 15.7 g (yield 78%) of N-(2-methoxyphenylacetyl)-anthranilic acid methyl ester.

m.p.: 116°–117° C.

EXAMPLE 1

2-(2-Methoxyphenylmethyl)-3-(2-diethylaminoethyl)-4(3H)-quinazolinone hydrochloride (Compound No. 1; Synthesis process A)

A solution of 3.0 g (10 mmol) of methyl ester of N-(2-methoxyphenyl-acetyl)-anthranilic acid and 5.1 g (50 mmol) of 2-diethylaminoethylamine in ethanol (20 ml) was heated at 180° C. for 7 hours in a seald tube. After cooling, the thus obtained reaction mixture was purified by silica gel column chromatography (eluent; chloroform : ethanol=98:2) to obtain 1.24 g (yield 34 %) of 2-(2-methoxyphenylmethyl)-3-(2-diethylaminoethyl)-4(3H)-quinazolinone as an oily substance. 1.2 g of the oily substance were dissolved in ethanol (5 ml) and a 7% HCl-ethanol solution (1.5 ml) were added thereto. The resulting solution was allowed to cool overnight. The resulting colorless precipitates were collected by filtration to obtain 1.0 g of the captioned hydrochloride which is the desired compound.

m.p.: 196°–209° C. (decomposition)

Infrared absorption spectrum (IR) (cm$^{-1}$): 1670 (C=O), 1590 (phenyl group)

Analysis Calculated for $C_{22}H_{27}N_3O_2$ HCl: C, 65.74; H, 6.77; N, 10.46%; Found: C, 65.57; H, 7.01; N, 10.44%.

EXAMPLES 2 to 29

2-(Substituted phenylmethyl)-3-(substituted aminoalkyl)-4 (3H)-quinazolinone derivatives (Compound Nos. 2 to 29)

The captioned compounds were synthsized in the same manner as in Example 1 except that the methyl ester of N-(2-methoxyphenylacetyl)anthranilic acid was replaced by corresponding esters of anthranilic acid, and the 2-diethylaminoethylamine was replaced by the corresponding diamines. The results obtained are shown in Table 1.

TABLE 1

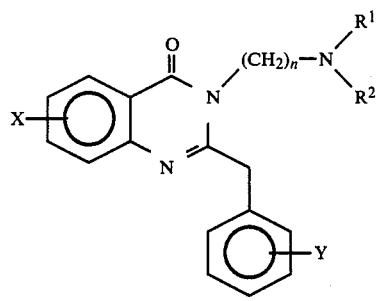

| Example No. | Compound No. | X | Y | $\begin{array}{c}R^1\\ N\\ R^2\end{array}$ | n | Discrimination between free base and salt | Ester form of starting material | Yield (%) | Melting point (°C.) | Infrared absorption spectrum (cm$^{-1}$) |
|---|---|---|---|---|---|---|---|---|---|---|
| 2 | 2 | hydrogen atom | 2-chloro | diethylamino | 2 | hydrochloride | ethyl | 57 | 188–193 | 1665 1590 |
| 3 | 3 | " | 4-chloro | " | 2 | " | methyl | 10 | 175–178 | 1670 1585 |
| 4 | 4 | " | 2-chloro | " | 2 | " | ethyl | 36 | 191–194 | 1670 1590 |
| 5 | 5 | " | 3-chloro | " | 2 | " | methyl | 36 | 210–213 | 1675 1590 |
| 6 | 6 | " | 4-chloro | " | 2 | fumarate | ethyl | 14 | 160–165 | 1675 1590 |
| 7 | 7 | " | 4-bromo | " | 2 | free base | methyl | 27 | (oily) | 1670 1590 |
| 8 | 8 | " | 4-methoxy | " | 2 | " | ethyl | 61 | (oily) | 1670 1590 |
| 9 | 9 | " | 2-ethoxy | " | 2 | hydrochloride | methyl | 17 | 159–162 | 1665 1585 |
| 10 | 10 | " | 4-ethoxy | " | 2 | " | " | 42 | 173–184 | 1670 1585 |
| 11 | 11 | " | 4-methyl | " | 2 | " | ethyl | 62 | 162–168 | 1660 1590 |
| 12 | 12 | " | 4-nitro | " | 2 | free base | " | 9 | 114–122 | 1665 1585 |
| 13 | 13 | " | 2,5-dimethoxy | " | 2 | hydrochloride | " | 42 | 179–181 | 1670 1590 |
| 14 | 14 | " | " | " | 3 | " | methyl | 8 | 120–124 | 1675 1590 |
| 15 | 15 | " | " | pyrrolidino | 2 | " | " | 25 | 124–128 | 1670 1585 |
| 16 | 16 | " | " | dimethylamino | 2 | " | " | 23 | 189–194 | 1660 1580 |
| 17 | 17 | " | " | " | 3 | " | " | 14 | 212–216 | 1665 1595 |
| 18 | 18 | " | 3,4-dimethoxy | diethylamino | 2 | free base | ethyl | 77 | (oily) | 1660 1585 |
| 19 | 19 | " | 2-benzyloxy | " | 2 | hydrochloride | methyl | 30 | 182–189 | 1665 1585 |
| 20 | 20 | " | 4-benzyloxy | " | 2 | " | " | 45 | 137–138 | 1670 1590 |
| 21 | 21 | 6-methyl | 2,5-dimethoxy | " | 2 | " | " | 13 | 152–155 | 1660 1580 |
| 22 | 22 | " | " | " | 3 | free base | " | 20 | (oily) | 1660 1580 |
| 23 | 23 | " | " | morpholino | 3 | " | " | 24 | " | 1665 1585 |
| 24 | 24 | " | " | dimethylamino | 2 | hydrochloride | " | 13 | 187–198 | 1655 1575 |
| 25 | 25 | 6-iodo | 2-methoxy | diethylamino | 2 | " | " | 54 | 189–194 | 1670 1585 |
| 26 | 26 | " | 2,5-dimethoxy | " | 2 | " | " | 49 | 164–168 | 1670 1585 |
| 27 | 27 | " | 4-ethoxy | " | 2 | " | " | 60 | 193–195 | 1670 1580 |
| 28 | 28 | 6-chloro | 2,5-dimethoxy | " | 2 | " | " | 44 | 162–163 | 1670 1585 |
| 29 | 29 | 7-chloro | " | " | 2 | " | " | 46 | 146–150 | 1680 1590 |

Synthesis example 2

2-(2,5-Dimethoxyphenylmethyl)-6-isopropoxy-4H-3,1,-benzoxazin-4-one

To a suspension of 9.8 g (50 mmol) of 5-isopropoxy-2-aminobenzoic acid and 11.0 g (80 mmol) of potassium carbonate in a mixed solvent of acetone (40 ml) and water (40 ml), 10.5 g (50 mmol) of 2,5-dimethoxyphenylacetic acid chloride were added dropwise at 10° C. After the resulting reaction mixture was stirred under ice cooling for 1 hour, stirring was continued for further 2 hours at room temperature. The thus obtained solution was made acidic with conc. hydrochloric acid and extracted with dichloromethane. After the extract was dried over magnesium sulfate, the solvent was distilled off to obtain 14.0 g (75%) of 2-(2,5-dimethoxyphenylacetylamino)-5-isopropoxybenzoic acid (m.p. 132°–135° C.). Then the thus obtained acid was heated under reflux for 2 hours in acetic anhydride (100 ml), followed by concentration under reduced pressure. The resulting residue was purified by silica gel column chromatography (eluent: dichloromethane) to obtain 6.8 g of 2-(2,5-dimethoxyphenylmethyl)-6-isopropoxy-4H-3,1-benzoxazine-4-one (yield from 5-isopropoxy-2-aminobenzoic acid: 36%)

m.p. 84°–87° C.
Infrared absorption spectrum (cm$^{-1}$): 1745, 1630

EXAMPLE 30

2-(2,5-Dimethoxyphenylmethyl)-3-(3-dimetylaminopropyl)-6-isopropoxy-4(3H)-quinazolinone maleate (Compound No. 30; Synthesis process B)

2.84 g (8 mmol) of 2-(2,5-dimethoxyphenylmethyl)-6-isopropoxy-4H-3,1-benzoxazin-4-one and 0.82 g (8 mmol) of 3-dimethylaminopropylamine were heated under reflux for 15 hours in xylene (20 ml). After the xylene was distilled off, the residue obtained was purified by silica gel column chromatography (eluent; 2% ethanol/chloroform) to obtain 1.46 g (42%) of 2-(2,5-dimethoxyphenylmethyl)-3-(3-dimethylaminopropyl)-6-isopropoxy-4(3H)-quinazolinone as an oily substance. Subsequently, 0.22 g of the 2-(2,5-dimethoxyphenylmethyl)-3-(3-dimethylaminopropyl)-6-isopropoxy-4(3H)-quinazolnone was dissolved in ether (15 ml) and to the resulting soluion, there was added an ethanolic solution containing 0.07 g (0.6 mmol) of maleic acid. The thus obtained solution was allowed to stand for one day. The precipitated colorless crystals were collected by filtration to obtain 0.25 g of the maleate which is the desired compound.

m.p.: 188°–189° C.
Mass spectrum (m/e): 439 (M+), 58 (Base peak ion)
Analysis Calculated for $C_{25}H_{33}N_3O_4 \cdot C_4H_4O_4$: C, 62.68; H, 6.71; N, 7.56%. Found: C, 62.48; H, 6.71; N, 7.57%.

EXAMPLES 31 to 88

2-(Substituted phenylmethyl)-3-(substituted aminoalkyl)-4 (3H)-quinazolinone derivatives, (Compound Nos. 31 to 88)

The captioned compounds were synthsized in the same manner as in Example 30 except that the 2-(2,5-dimethoxyphenylmethyl)-6-isopropoxy-4H-3,1-benzoxazin-4-one was replaced by the corresponding 4H-3,1-benzoxazin-4-one, and the 3-dimethylaminopropylamine was replaced by the corresponding diamines. The results obtained are shown in Table 2.

TABLE 2

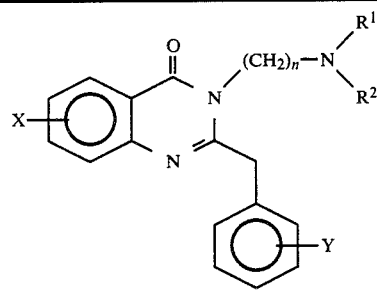

| Example No. | Compound No. | X | Y | N R¹/R² | n | Discrimination between free base and salt | Yield (%) | Melting point (°C.) | M+ | Base peak ion |
|---|---|---|---|---|---|---|---|---|---|---|
| 31 | 31 | 6-methyl | 2,5-dimethoxy | pyrrolidino | 2 | fumarate | 75 | 169–170 | 407 | 84 |
| 32 | 32 | " | " | " | 3 | free base | 54 | oily | 421 | 84 |
| 33 | 33 | 6-ethyl | " | dimethylamino | 3 | " | 50 | " | 409 | 58 |
| 34 | 34 | " | " | diethylamino | 3 | " | 48 | " | 437 | 86 |
| 35 | 35 | 7-chloro | " | dimethylamino | 3 | hydrochloride | 90 | 186–192 | 415 | 58 |
| 36 | 36 | " | " | pyrrolidino | 3 | free base | 45 | oily | 441 | 84 |
| 37 | 37 | " | " | diethylamino | 3 | " | 68 | " | 443 | 86 |
| 38 | 38 | 6-hydroxy | " | pyrrolidino | 2 | " | 38 | " | 409 | 84 |
| 39 | 39 | " | " | dimethylamino | 3 | " | 38 | " | 397 | 58 |
| 40 | 40 | 6-methoxy | " | " | 3 | " | 5 | " | 411 | 58 |
| 41 | 41 | 6-ethoxy | 2-methoxy | " | 2 | hydrochloride | 83 | 209–216 | 381 | 58 |
| 42 | 42 | " | 4-methoxy | " | 2 | " | 83 | 235–240 | 381 | 58 |
| 43 | 43 | " | 2,5-dimethoxy | " | 2 | " | 83 | 214–217 | 411 | 58 |
| 44 | 44 | 6-n-propoxy | " | pyrrolidino | 2 | " | 69 | 132–137 | 416 | 84 |
| 45 | 45 | " | " | diethylamino | 2 | " | 82 | 154–159 | 453 | 86 |
| 46 | 46 | 6-isopropoxy | " | pyrrolidino | 2 | " | 32 | 141–147 | 451 | 84 |
| 47 | 47 | " | " | dimethylamino | 2 | " | 61 | 184–188 | 425 | 58 |
| 48 | 48 | " | " | diethylamino | 2 | " | 76 | 154–158 | 453 | 86 |
| 49 | 49 | " | " | pyrrolidino | 3 | " | 48 | 125–130 | 465 | 84 |
| 50 | 50 | " | 4-methoxy | dimethylamino | 2 | " | 46 | 195–199 | 395 | 58 |
| 51 | 51 | " | 2-chloro | " | 2 | free base | 50 | oily | 399 | 58 |
| 52 | 52 | " | 4-chloro | " | 2 | " | 51 | " | 389 | 58 |
| 53 | 53 | " | 4-methoxy | " | 3 | " | 35 | " | 409 | 58 |
| 54 | 54 | 6-n-butoxy | 2,5-dimethoxy | " | 3 | hydrochloride | 51 | 184–188 | 453 | 58 |
| 55 | 55 | " | " | pyrrolidino | 2 | " | 89 | 166–173 | 465 | 84 |
| 56 | 56 | " | " | diethylamino | 2 | " | 53 | 150–157 | 468 | 86 |
| 57 | 57 | " | " | dimethylamino | 2 | " | 83 | 130–138 | 439 | 58 |
| 58 | 58 | 6-isobutoxy | " | pyrrolidino | 2 | " | 33 | 154–161 | 465 | 84 |
| 59 | 59 | " | " | dimethylamino | 3 | free base | 31 | oily | 453 | 58 |
| 60 | 60 | 6-sec-butoxy | " | " | 3 | " | 31 | " | 453 | 58 |
| 61 | 61 | " | " | pyrrolidino | 2 | hydrochloride | 57 | 147–153 | 465 | 84 |
| 62 | 62 | " | " | diethylamino | 2 | free base | 19 | oily | 467 | 86 |
| 63 | 63 | " | " | dimethylamino | 2 | hydrochloride | 92 | 116–125 | 439 | 58 |
| 64 | 64 | " | " | " | 3 | " | 71 | 185–190 | 453 | 58 |
| 65 | 65 | 6-n-pentoxy | " | " | 3 | " | 72 | 210–214 | 467 | 58 |
| 66 | 66 | " | " | pyrrolidino | 2 | " | 68 | 127–135 | 479 | 84 |
| 67 | 67 | " | " | " | 3 | free base | 60 | oily | 493 | 84 |
| 68 | 68 | " | " | dimethylamino | 3 | " | 63 | " | 495 | 86 |
| 69 | 69 | " | " | " | 2 | hydrochloride | 59 | 123–129 | 481 | 86 |
| 70 | 70 | " | " | " | 2 | " | 70 | 141–150 | 453 | 58 |
| 71 | 71 | 6-isopentoxy | " | pyrrolidino | 2 | " | 82 | 140–148 | 479 | 84 |
| 72 | 72 | " | " | " | 3 | " | 59 | 99–103 | 493 | 84 |
| 73 | 73 | " | " | dimethylamino | 3 | free base | 56 | oily | 467 | 58 |
| 74 | 74 | " | " | " | 2 | hydrochloride | 65 | 129–137 | 453 | 58 |
| 75 | 75 | " | " | diethylamino | 2 | " | 63 | 131–138 | 481 | 86 |

TABLE 2-continued

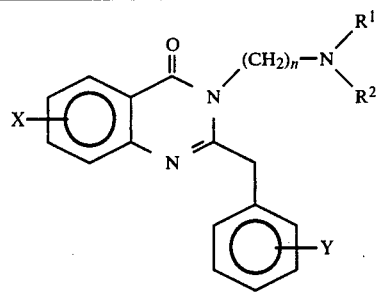

| Example No. | Compound No. | X | Y | $N{<}^{R^1}_{R^2}$ | n | Discrimination between free base and salt | Yield (%) | Melting point (°C.) | M+ | Base peak ion |
|---|---|---|---|---|---|---|---|---|---|---|
| 76 | 76 | " | " | " | 3 | free base | 43 | oily | 495 | 86 |
| 77 | 77 | 6,7-dimethoxy | " | dimethylamino | 2 | " | 64 | " | 427 | 58 |
| 78 | 78 | " | 4-methoxy | " | 2 | " | 73 | " | 397 | 58 |
| 79 | 79 | 6-methoxy-7-isopropoxy | 2,5-dimethoxy | " | 2 | " | 62 | " | 455 | 58 |
| 80 | 80 | 6-methoxy-7-isopropoxy | 4-methoxy | " | 2 | " | 45 | " | 425 | 58 |
| 81 | 81 | 6-isopropoxy-7-methoxy | 2,5-dimethoxy | " | 2 | " | 77 | 115–118 | 455 | 58 |
| 82 | 82 | 6-isopropoxy-7-methoxy | 4-methoxy | " | 2 | hydrochloride | 58 | 235–239 | 425 | 58 |
| 83 | 83 | 6-isopropoxy-7-methoxy | " | methylamino | 2 | free base | 28 | oily | 411 | 355 |
| 84 | 84 | 6-ethoxy-7-methoxy | " | dimethylamino | 2 | " | 77 | " | 411 | 58 |
| 85 | 85 | 6-ethoxy-7-methoxy | " | " | 3 | " | 77 | " | 425 | 58 |
| 86 | 86 | 6-isopropoxy | 2-methoxy | " | 2 | hydrochloride | 70 | 178–183 | 395 | 58 |
| 87 | 87 | 6-isopropoxy-7-methoxy | " | " | 2 | " | 97 | 200–203 | 425 | 58 |
| 88 | 88 | 6-phenoxy | 2,5-dimethoxy | " | 2 | " | 49 | 184–187 | 459 | 58 |

Synthesis example 3

2-(2-Methoxyphenylmethyl)-4H-3,1-benzoxazin-4-one

Following the same procedure as in Synthesis example 2, 2-(2-methoxyphenylmethyl)-4H-3,1-benzoxazin-4-one was obtained from anthranilic acid and 2-(methoxyphenylacetic acid chloride as starting materials via 2-(2-methoxyphenylmethylcarbonyl amino)benzoic acid as an intermediate (yield: 60%).

m.p. 102°–104° C.

Mass spectrum (m/e): 267 (M+), 146 (Base peak ion)
Infrared absorption spectrum (cm$^{-1}$): 1740, 1635, 1595

EXAMPLE 89

2-(2-Methoxyphenylmethyl)-3-[2-{N-(3,4-dimethoxyphenylethyl)-N-methylamino}ethyl]-4(3H)-quinazolinone hydrochloride (Compound No. 89; Synthesis process B)

268 mg (1 mmol) of 2-(2-methoxyphenylmethyl)-4H-3,1-benzoxazine-4-one and 238 mg (1 mmol) of 2-[[N-[2-(3,4-dimethoxyphenyl)ethyl]-N-methylamino]]ethylamine were heated in xylene (10 ml) under reflux for 10 hours. After the xylene was distilled off, the residue obtained was purified by silica gel column chromatography (eluent; 2% ethanol/chloroform) to obtain 107 mg (52%) of 2-(2-methoxyphenylmethyl)-3-[2-{N-(3,4-dimethoxyphenylethyl)-N-methylamino}ethyl]-4(3H)-quinazolinone as an oily substance. Subsequently, the thus obtained quinazolinone was dissolved in ethanol (2 ml) and to the resulting soluion there was added a 7% hydrogen chloride-ethanol solution (1 ml). Further, ether was added to the reaction mixture thus obtained, and the precipitated colorless crystals were collected by filtration to obtain 99 mg of the hydrochloride which is the desired compound.

m.p.: 171°–175° C. (decomposition)

Mass spectrum (m/e): 487 (M+), 293 (Base peak ion)
Analysis Calculated for $C_{29}H_{33}N_3O_4 \cdot HCl$: C, 66.46; H, 6.54; N, 8.02%;
Found: C, 66.23; H, 6.75; N, 7.89%.

EXAMPLES 90 to 132

2-(Substituted phenylmethyl)-3-[N-alkyl-N-(substituted phenylalkyl)aminoalkyl]-4(3H)-quinazolinone derivatives (Compound Nos. 90 to 132)

The captioned compounds were synthsized in the same manner as in Example 89 except that the 2-(2-methoxyphenylmethyl)-4H-3,1-benzoxazin-4-one was replaced by the corresponding 4H-3,1-benzoxazin-4-one derivatives, and the 2-[N-{2-(3,4-dimethoxyphenyl)ethyl}-N-methylamino]ethylamine was replaced by the corresponding N-alkyl-N-(substituted phenylalkyl)aminoalkylamines. The results obtained are shown in Table 3.

TABLE 3

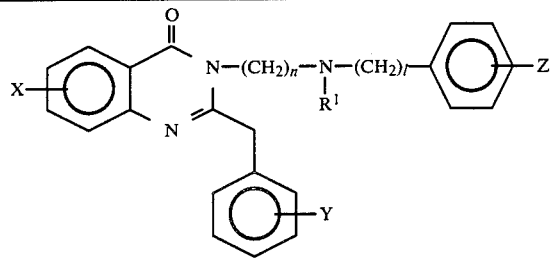

| No. | No. | X | Y | R¹ | Z | n | l | Discrimination between free base and salt | Yield (%) | Melting point (°C.) | Mass spectrum (m/e) M⁺ | Base peak ion |
|---|---|---|---|---|---|---|---|---|---|---|---|---|
| 90 | 90 | hydrogen atom | 2-methoxy | methyl | hydrogen atom | 2 | 2 | hydrochloride | 51 | 180–210 | 427 | 293 |
| 91 | 91 | " | " | " | " | 2 | 1 | " | 50 | 175–185 | 413 | 134 |
| 92 | 92 | " | " | " | " | 3 | 2 | free base | 57 | oily | 441 | 307 |
| 93 | 93 | " | 2,5-dimethoxy | " | 3,4-dimethoxy | 2 | 2 | " | 23 | " | — | 337 |
| 94 | 94 | " | 4-chloro | " | hydrogen atom | 2 | 2 | hydrochloride | 42 | 180–190 | 431 | 297 |
| 95 | 95 | " | 2-methyl | " | " | 2 | 2 | free base | 53 | oily | 411 | 277 |
| 96 | 96 | " | 3-methyl | " | " | 2 | 2 | " | 45 | " | 411 | 277 |
| 97 | 97 | " | 2-isoproxy | " | " | 2 | 2 | " | 43 | " | 455 | 321 |
| 98 | 98 | " | 2-methoxy | " | " | 2 | 3 | " | 75 | " | 441 | 293 |
| 99 | 99 | " | " | " | " | 2 | 4 | hydrochloride | 44 | 132–140 | 455 | 176 |
| 100 | 100 | " | " | ethyl | " | 2 | 2 | free base | 72 | oily | 441 | 162 |
| 101 | 101 | " | " | buthyl | " | 2 | 2 | " | 19 | " | 469 | 293 |
| 102 | 102 | 6-isopropoxy | 2,5-dimethoxy | methyl | 3,4-dimethoxy | 2 | 2 | " | 14 | " | 575 | 381 |
| 103 | 103 | " | " | " | " | 3 | 2 | " | 11 | " | 589 | 395 |
| 104 | 104 | " | " | " | hydrogen atom | 3 | 2 | " | 9 | " | 529 | 395 |
| 105 | 105 | 6-sec-butoxy | " | " | 3,4-dimethoxy | 2 | 2 | " | 29 | " | — | 265 |
| 106 | 106 | 6-(4-chlorophenoxy) | " | " | " | 2 | 2 | hydrochloride | 36 | 106–111 | 643 | 449 |
| 107 | 107 | 6-(4-methoxyphenoxy) | " | " | " | 2 | 2 | " | 23 | 100–106 | 639 | 445 |
| 108 | 108 | hydrogen atom | " | " | " | 3 | 2 | free base | 37 | oily | 531 | 265 |
| 109 | 109 | 6-n-butoxy | " | " | " | 2 | 2 | " | 33 | " | 589 | 395 |
| 110 | 110 | 6-n-pentoxy | " | " | " | 2 | 2 | " | 29 | " | 603 | 409 |
| 111 | 111 | 6-isopentoxy | " | " | " | 2 | 2 | " | 26 | " | 603 | 409 |
| 112 | 112 | hydrogen atom | 4-methoxy | " | " | 2 | 2 | " | 31 | " | 487 | 293 |
| 113 | 113 | " | 2-chloro | " | " | 2 | 2 | " | 17 | " | — | 297 |
| 114 | 114 | 6-methyl | 2,5-dimethoxy | " | " | 2 | 2 | " | 21 | " | 531 | 337 |
| 115 | 115 | hydrogen atom | 3,4-dimethoxy | " | " | 2 | 2 | " | 43 | " | 517 | 323 |
| 116 | 116 | 6-iodo | 2,5-dimethoxy | " | " | 2 | 2 | " | 56 | " | 643 | 449 |
| 117 | 117 | 6-isopropoxy | 2-methoxy | " | " | 2 | 2 | " | 37 | " | 545 | 351 |
| 118 | 118 | " | 4-methoxy | " | " | 2 | 2 | " | 37 | " | 545 | 351 |
| 119 | 119 | " | 2-chloro | " | " | 2 | 2 | " | 40 | " | 549 | 355 |
| 120 | 120 | " | 3,4-dimethoxy | " | " | 2 | 2 | " | 51 | " | 575 | 381 |
| 121 | 121 | 6-ethoxy | 2,5-dimethoxy | " | " | 2 | 2 | " | 22 | " | 561 | 367 |
| 122 | 122 | 6-methoxy | " | " | " | 2 | 2 | " | 51 | " | 547 | 353 |
| 123 | 123 | hydrogen atom | " | " | 3-methoxy | 2 | 2 | " | 14 | " | 487 | 323 |
| 124 | 124 | 6-isopropoxy | " | " | " | 2 | 2 | " | 13 | " | 545 | 381 |
| 125 | 125 | hydrogen atom | " | " | 4-methyl | 2 | 2 | " | 22 | " | 471 | 323 |
| 126 | 126 | 6-isopropoxy | " | " | " | 2 | 2 | " | 18 | " | 529 | 381 |
| 127 | 127 | " | " | " | 4-methoxy | 2 | 2 | " | 28 | " | 545 | 381 |
| 128 | 128 | hydrogen atom | " | " | 4-chloro | 2 | 2 | " | 20 | " | 491 | 323 |
| 129 | 129 | 6-isopropoxy | " | " | " | 2 | 2 | " | 9 | " | 549 | 381 |
| 130 | 130 | hydrogen atom | " | " | 2,5-dimethoxy | 2 | 2 | " | 26 | " | 517 | 323 |
| 131 | 131 | 6-isopropoxy | " | " | " | 2 | 2 | " | 17 | " | 575 | 381 |
| 132 | 132 | hydrogen atom | " | " | 4-methoxy | 2 | 2 | " | 48 | " | 487 | 323 |

Synthesis example 4

2-(2,5-Dimethoxyphenylacetylamino)-5-methyl-N-(2-dimethylaminoethyl)benzamide 0.50 g (1.5 mmol) of 2-(2,5-dimethoxyphenylacetylamino)-5-methylbenzoic acid (m.p. 163 to 164.5° C.) synthesized in the same manner as in Synthesis example 1 for 2-(2,5-dimethoxyphenylacetylamino)-5-isopropoxybenzoic acid was suspended in dichloromethane (10 ml), and then to the resulting mixture was added dropwise a dichloromethane solution containing 0.33 (1.6 mmol) of dicyclohexylcarbodiimide (DCC) under ice cooling. Subsequently, 0.14 g (16 mmol) of 2-dimethylaminoethylamine was added dropwise thereto and the mixture thus obtained was stirred for 2 hours at room temperature. The precipitates were filtered off and the mother liquid was concentrated by distillation. The thus obtained residue was purified by silica gel column chromatography (eluent; dichloromethane:ethanol=97:3) to obtain 0.41 g (yield 68%) of 2-(2,5-dimethoxyphenylacetyamino)-5-methyl-N-(2-dimethylaminoethyl)benzamide.

m.p. 105°–110° C.

EXAMPLE 133

2-(2,5-Dimethoxyphenylmethyl)-3-(2-dimethylaminoethyl)-6-methyl-4(3H)-quinazolinone hydrochloride (Compound No. 24; Synthesis process C)

0.37 g (1 mmol) of 2-(2,5-dimethoxyphenylacetylamino)-N-(2-dimethylaminoethyl)benzamide and 200 mg of para-toluenesulfonic acid were heated in xylene (20 ml) under reflux for 3 hours. The reation mixture thus obtained was purified by silica gel column chromatography (eluent; 2 % ethanol/chloroform) to obtain 70 mg (20 %) of 2-(2,5-dimethoxyphenylmethyl)-3-(2-dimethylaminoethyl) -6-methyl-4(3H)-quinazolinone as an oily substance. Subsequently, the thus obtained oily substance was dissolved in 1 ml of ethanol, and to the resulting solution was added a 7 % hydrogen chloride-ethanol solution (2 ml). Further, ether was added to the reaction mixture thus obtained and the precipitated colorless crystals were collected by filtration to obtain 70 mg of the hydrochloride which is the desired compound. The melting point and infrared absorption spectrum of the above hydrochloride was identical with those of Compound 24 synthesized in Example 24, respectively.

Synthesis example 5

2-(2-Methoxyphenylmethyl)-3-(2-chloroethyl)-4(3H)-quinazolinone

A suspension of 3.0 g (10 mmol) of methyl ester of N-(2-methoxyphenylacetyl)anthranilic acid and 1.2g (20 mmol) of monoethanolamine in xylene was heated at 180° C. for 16 hours in a sealed tube. After cooling, the precipitated crystals were collected by filtration to obtain 0.7 g (22%) of 2-(2-methoxyphenylmethyl)-3-(2-hydroxyethyl)- 4(3H)-quinazolinone (m.p.: 154°–155° C.). Subsequently, to 0.7 g (2.2 mmol) of this 3-(2-hydroxyethyl) derivative was added thionyl chloride (5 ml) and the resulting reaction mixture was stirred at room temperature for 1 hour. An excess of the thionyl chloride was distilled off under reduced pressure and the resulting residue was purified by silica gel column chromatography (eluent:dichloromethane) to obtain 0.14 g (20%) of 2-(2-methoxyphenylmethyl)-3-(2-chloroethyl)-4(3H)-quinazolinone. (m.p.: 109°–111° C.).

EXAMPLE 134

2-(2-Methoxyphenylmethyl)-3-(2-ethylaminoethyl)-4(3H)-quinazolinone (Compound No. 133; Synthesis process D)

A mixture of 328 mg (1 mmol) of 2-(2-methoxyphenylmethyl) -3-(2-chloroethyl)-4(3H)-quinazolinone and a 70% aqueous ethylamine solution (0.6 ml) in ethanol (10 ml) was heated at 80 ° C. W for 8 hours in a sealed tube. The solvent was distilled off under reduced pressure and to the residue thus obtained there was added a 10 % aqueous potassium carbonate solution, followed by extraction with dichloromethane. The thus obtained dichloromethane solution was dried over magnesium sulfate and then concentrated. The resulting residue was purified by silica gel column chromatography (eluent: 1% ethanol-chloroform) to obtain 55 mg (16%) of 2-(2-methoxyphenylmethyl)-3-(2-ethylaminoethyl)-4(3H)-quinazolinone as an oily substance. Subsequently, the thus obtained quinazolinone was dissolved in ether (3 ml) and to the resulting solution was added a 10% HCl/ethanol solution. The precipitated crystals were collected by filtration to obtain the hydrochride of the captioned compound.

m.p.: 170°–175° C.

Mass spectrum (m/e): 337 (M+), 267 (Base peak ion)

EXAMPLES 135 to 136

2-(2-Methoxyphenylmethyl)-3-(substitued aminoalkyl)-4(3H)-quinazolinone derivatives (Compound Nos. 134 and 135)

The captioned compounds were synthesized in the same manner as in Example 134 except that the 70 % aqueous ethylamine solution was replaced by the corresponding amines, respectively. The results obtained are shown in Table 4.

TABLE 4

| Example No. | Compound No. | X | Y | N$\begin{array}{c}R^1\\R^2\end{array}$ | n | Discrimination between free base and salt | Yield (%) | Melting point (°C.) | Mass spectrum (m/e) M+ | Base peak ion |
|---|---|---|---|---|---|---|---|---|---|---|
| 135 | 134 | hydrogen atom | 2-methoxy | cyclopentylamino | 2 | free base | 41 | oily | 377 | 267 |
| 136 | 135 | " | " | hexamethyleneimino | 2 | hydrochloride | 50 | 135–145 | — | 112 |

Synthesis example 6

2-(2,5-dimethoxyphenylmethyl)-6-methyl-4(3H)-quinazolinone

A mixture of 3.15 g (9.6 mmol) of 2-(2,5-dimethoxyphenylacetylamino)5-methylbenzoic acid (m.p. 163° to 164.5° C.) obtainble by the same method as in Synthesis example 2 and 0.90 g (20ml) of formamide were heated at 160° C. for 3 hours. After cooling, the solidified residue was added to a mixed solution of ethanol (100 ml) and acetone (100 ml) and dissolved therein by heating. After cooling, the precipitated crystals were collected by filtration to obtain 1.45 g (yield 49 %) of 2-(2,5-dimethoxyphenylmethyl)-6-methyl-4(3H)-quinazolinone.

m.p.: 188°–189° C.

Mass spectrum (m/e): 310 (M+), 279 (Base peak ion)

EXAMPLE 138

2-(2,5-Dimethoxyphenylmethyl)-3-(2-dimethylaminoethyl)-6-methyl-4(3H)-quinazolinone hydrochloride (Compound No. 24; Synthesis process E)

A suspension of 0.62 g (2 mmol) of 2-(2,5-dimethoxyphenylmethyl)-6-methyl-4(3H)-quinazolinone and 0.19 g (2 mmol) of 50% sodium hydride in dioxane (10 ml) were stirred at room temperature for 1 hour. Then, to the resulting reaction mixture was added 0.22 g (2 mmol) of dimethylaminoethyl chloride dissolved in dioxane (10 ml), followed by heating at 60° C. for 5 hours. After cooling, to the mixture obtained were added 30 ml of water. The resulting mixture was extracted with dichloromethane and the dichloromethane layer was concentrated under reduced pressure. The thus obtained residue was purified by silica gel column chromatography (eluent; dichloromethane: ethanol=97:3) to obtain 0.10 g (yield 13 %) of 2-(2,5-dimethoxyphenylmethyl)-3-(2-dimethylaminoethyl)-6-methyl-4(3H)-quinazolinone as an oily substance. The thus obtained quinazolinone was dissolved in ether and to the resulting solution was added a 5% hydrogen chloride-ethanol solution and the precipitated crystals were collected by filtration to obtain 2-(2,5-dimethoxyphenylmethyl)-3-(2-dimethylaminoethyl)-6-methyl-4(3H)-quinazolinone hydrochloride. The melting point and infrared absorption spectrum of this hydrochloride were identical with those of Compound 24 obtained in Example 24, respectively.

EXAMPLE 139

2-(2,5-Dimethoxyphenylmethyl)-3-{2-(1-pyrrolidino)ethyl}-6-benzyloxy-4(3H)-quinazolinone (Compound No. 136)

2-(2,5-dimethoxyphenylmethyl)-3-{2-(1-pyrrolidino)ethyl}-6 -hydroxy-4(3H)-quinazolinone (Compound No. 38) (90 mg, 0.2 mmol) and sodium hydroxide (16 mg, 0.4 mmol) were added to a mixed solvent of ethanol (10 ml) and water (5 ml). To the resulting reaction mixture were added benzyl chloride (40 mg, 0.3 mmol), followed by reflux for 1 hour, and then, to the mixture thus obtained further were added benzyl chloride (27 mg, 0.2 mmol), followed by reflux for further 1.5 hours. After concentration under reduced pressure, water was added thereto and the mixture obtained was extracted with dichloromethane. The dichloromethane solution was dried over magnesium sulfate and purified by silica gel column chromatography {eluent; ethanol (0–5%)-dichloromethane} to obtain 16 mg (15%) of 2-(2,5-dimethoxyphenylmethyl)-3-{2-(1-pyrrolidino) ethyl}-6-benzyloxy-4(3H)-quinazolinone.

Mass spectrum (m/e): 499 (M+), 84 (Base peak ion)
Infrared absorption spectrum (IR) (cm$^{-1}$): 1655, 1585

EXAMPLE 140

3-(2-Dimethylaminoethyl)-2-{2-(4-methoxyphenyl)ethyl}-4 (3H)-quinazolinone (Compound No. 137; Synthesis process B)

A mixture of 295 mg (1 mmol) of 2-{2-(4-methoxyphenyl)ethyl}-4H-3,1-benzoxazin-4-one synthesized in the same manner as in Synthesis example 2 and 88 mg (1 mmol) of 2-dimethylaminoethylamine in xylene (5 ml) was heated under reflux for 2 hours. After the xylene was distilled off under reduced pressure, the crude crystals obtained were purified by silica gel column chromatography (eluent; 3% methanol/methylene chloride) to obtain 260 mg (76%) of 3-(2-dimethylaminoethyl)-2-{2-(4-methoxyphenyl)ethyl}- 4(3H)-quinazolinone.

m.p.: 73.5°–74.5° C.
Mass spectrum (m/e): 351 (M+), 58 (Base peak ion)
Infrared absorption spectrum (IR) (cm$^{-1}$): 1665 (C=O), 1600 (phenyl group)

EXAMPLE 141

3-(2-Dimethylaminoethyl)-6-isopropoxy-7-methoxy-2-({3-(4-methoxyphenyl)propyl}-4(3H)-qunazolinone (Compound No. 138, 1 Synthesis process B)

A mixture of 384 mg (1 mmol) of 6-isopropoxy-7-methoxy-2-({3-(4-methoxyphenyl)propyl}4H-3,1-benzoxazin-4-one synthesized in the same manner as in Synthesis example 2 and 88 mg (1 mmol) of 2-dimethylaminoethylamine in xylene (5 ml) was heated under reflux for 2 hours. After the xylene was distilled off, the crude crystals obtained were purified by silica gel column chromatography (eluent; 3% methanol/methylene chloride) to obtain 362 mg (80 %) of 3-(2-dimethylaminoethyl)-6-isopropoxy-7-methoxy-2-{3-(4-methoxyphenyl)propyl}-4(3H)-quinazolinone.

m.p.: 65.5°–66.5° C.
Mass spectrum (m/e): 453 (M+), 58 (Base peak ion)
m.p.: 65.5°–66.5° C.
Mass spectrum (m/e): 453 (M+), 58 (Base peak ion)
Infrared absorption spectrum (IR) (cm$^{-1}$): 1660 (C=O), 1605 (phenyl group)

EXAMPLE 142

2-(2,5-Dimethoxyphenylmethyl)-3-(2-dimethylaminoethyl)-4 (3H)-quinazolinone hydrochloride (Compound No. 16; Synthesis process A)

A mixture of 0.62 g (2 mmol) of N-(2,5-dimethoxyphenylacetyl) anthranilic acid and 0.36 g (3 mmol) of 2-dimethylaminoethylamine in xylene (5 ml) were heated under reflux for 24 hours. After cooling, the resulting reaction mixture was purified by silica gel column chromatography (eluent; chloroform: ethanol=98:2) to obtain 0.10 g (yield 14%) of 2-(2,5-dimethoxyphenylmethyl)-3-(2-dimethylaminoethyl)-4(3H) quinazolinone as an oily substance. 0.10 g of the oily substance thus obtained was dissolved in ethanol (1 ml) and then a 7% HCl-ethanol solution (0.2 mol) was added thereto and the resulting reaction mixture was cooled overnight. The resulting colorless precipitates were collected by filtration to obtain 0.1 g of the hydrochloride which is the desired compound. This hydrochloride coincides with the compound obtained in Example 16 in melting point and infrared absorption spectrum.

Application example 1

Calcium antagonistic activity

Calcium antagonistic activity of the present compound was investigated by observing the effects on the calcium induced contraction of the isolated thoracic aorta in rats.

A piece of thoracic aorta was isolated from male Wistar strain rats weighing 350–450 g in order to prepare a spiral specimen. This specimen was suspended in a Krebs-Henseleit solution free from calcium. The contraction was evoked by an application of $CaCl_2$ in the presence of 80 mM potassium so as to adjust the solution at a concentration of 10 mM $Ca^{++}$. The present compound to be tested was applied to the specimen which had been maximally contracted and was evaluated for its relaxing activity. The results obtained are shown in Table 5.

TABLE 5

| Calcium antagonistic activity | |
|---|---|
| Compound No. | Minimum effective concentration (μM) |
| 1 | 1 |
| 13 | 3 |
| 14 | 1 |
| 15 | 0.3 |
| 19 | 0.3 |
| 20 | 0.3 |
| 26 | 1 |
| 30 | 0.3 |
| 31 | 1 |
| 47 | 0.1 |

TABLE 5-continued

| | Calcium antagonistic activity |
|---|---|
| Compound No. | Minimum effective concentration (μM) |
| 50 | 0.3 |
| 63 | 0.3 |
| 64 | 0.3 |
| 89 | 0.3 |
| 93 | 0.03 |
| 102 | 0.03 |
| 103 | 0.1 |
| 114 | 0.1 |
| 116 | 0.03 |
| 121 | 0.03 |
| diltiazem (Control) | 0.3 |

Application example 2

Increasing activity of coronary blood flow

Male and female mongrel dogs weighing 8 to 17.5 kg were anesthetized with intravenous administration of sodium pentobarbital at a dosage of 30 mg/kg. Under artificial respiration the chest was opened on the left side at the level of the fourth intercostal space and the heart was exposed. The circumflex branch of left coronary artery just below the junction of the anterior descending branch of left coronary artery was isolated in a width of approximately 1 cm, and a flow probe was placed around this artery in order to measure the blood flow of the circumflex branch of left coronary artery by means of an electromagnetic flow meter. During the tests, systemic blood pressure was monitored, and data obtained from tests where the mean blood presure was less than 65 mmHg were excluded from the final data. The pharmaceutical compound to be tested was dissolved in physiological saline or 50% ethanol/50% physiological saline and the thus obtained solution was intravenously administered at a dosage of 1 ml/10 kg through a polyethylene catheter which had been provided within the left femoral vein. The increasing activity of the blood flow of the circumflex branch of left coronary artery was evaluated and expressed in terms of increase rate of the blood flow after the administration of the compound to that of before the administration of the compound. The results obtained are shown in Table 6.

TABLE 6

| Increase in coronary blood flow (dog, 0.1 mg/kg iv) | |
|---|---|
| Compound No. | Increase rate of coronary blood flow (%) |
| 13 | 32.7 |
| 14 | 42.7 |
| 15 | 45.3 |
| 31 | 42.5 |
| 47 | 95.4 |
| 63 | 77.3 |
| 64 | 47.6 |
| 102 | 53.6 |
| diltiazem (Control) | 91.2 |

Application example 3

Antihypertensive activity

The compounds to be tested were administered orally to evaluate antihypertensive activity in spontaneously hypertensive rats (hereinafter SHR).

The average blood pressure of male SHR, 20 to 30 weeks old, was measured in a non-anestetised and non restraint state, through a catheter which had been chronically implanted into the abdominal aorta through the right fermoral artery, using an electromanometer. At the same time, the heart rate was measured by a tachometer triggered by the pulse pressure. The compound to be tested was suspended in a 1% tragacanth solution. After the concentration of the suspensions was adjusted in a volume of 5 ml/kg, the compound was administered orally to the SHR. The blood pressure and heart rate were measured 0.5, 1, 3, 6 and 24 hours after the administration. The results are shown in Table 7.

TABLE 7

| | | | Antihypertensive activity | |
|---|---|---|---|---|
| Comp. No. | Oral doasge (mg/kg) | Average blood pressure before administration | Increase rate of average blood pressure after administration (%) | |
| | | | after 1 hour | after 3 hours |
| 47 | 10 | 188 | −12 | −3 |
| 50 | 10 | 190 | −17 | −7 |
| 82 | 10 | 190 | −24 | −15 |
| 102 | 10 | 187 | −11 | −2 |
| diltiazem (Control) | 30 | 185 | −8 | 0 |
| | 100 | 186 | −28 | −14 |

Application example 4

Acute toxicity test

Tests were made using groups each comprising five male ICR strain mice weighing 30 to 35 g and being kept under a fast for 18 hours. The compound to be tested was suspended in a 1% tragacanth solution. After the concentration of the suspensions was adjusted in a volume of 40 ml/kg, the compound was administered orally to the mouse. The results are shown in Table 8.

TABLE 8

| Acute toxicity test (mouse, oral administration) | |
|---|---|
| Comp. No. | LD50 (mg/kg) |
| 13 | 700 |
| 31 | 1,000 |
| 47 | 750 |
| 50 | 700 |
| 63 | 1,200 |
| 82 | 750 |
| 102 | 1,000 |
| diltiazem (Control) | 650 |

We claim:

1. 2-Phenylalkyl-3-aminoalkyl-4(3H)-quinazolinone compound of Formula (1):

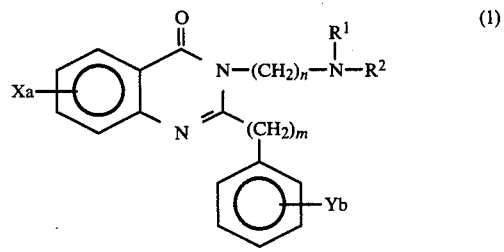

wherein, X represents a hydrogen atom, an alkyl group having 1 to 5 carbon atoms, an alkoxy group having 1 to 5 carbon atoms, a phenoxy group, a benzyloxy group, a halogen atom or a hydroxy group; Y represents an alkyl group having 1 to 5 carbon atoms, an alkoxy group having 1 to 5 carbon atoms, a benzyloxy group, a halogen atom or a nitro group; $R^1$ represents a hydrogen atom or an alkyl group having 1 to 5 carbon atoms; $R^2$ represents an alkyl group having 1 to 5 carbon atoms or a group of Formula (2)

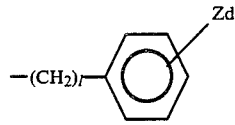

wherein, Z represents a hydrogen atom, an alkyl group having 1 to 5 carbon atoms, an alkoxy group having 1 to 5 carbon atoms or a halogen atom; d is an integer of 1 to 3; and l is an integer of 1 to 5; or $R^1$ and $R^2$ represent, together with the nitrogen atom to which they are attached, a cyclic amino group of the formula:

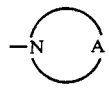

wherein, A represents an alkylene group having 2 to 6 carbon atoms or a group of the formula —(CH$_2$)$_2$—O—(CH$_2$)$_2$—; a and b are independently an integer of 1 to 3; and n and m are independently an integer of 1 to 5, or a pharmaceutically acceptable acid addition salt thereof.

2. The compound of Formula (1) according to claim 1, in which

X represents a hydrogen atom, a methyl group, an ethyl group, an n-propyl group, an isopropyl group, an n-butyl group, a sec-butyl group, a pentyl group, a methoxy group, an ethoxy group, an n-propoxy group, an isopropoxy group, an n-butoxy group, an sec-butoxy group, an n-pentoxy group, a phenoxy group, a benzyloxy group, a fluorine atom, a chlorine atom, a bromine atom, an iodine atom or a hydroxy group;

Y represents a methyl group, an ethyl group, an n-propyl group, an isopropyl group, an n-butyl group, a sec-butyl group, a pentyl group, a methoxy group, an ethoxy group, an n-propoxy group, an isopropoxy group, an n-butoxy group, a sec-butoxy group, an n-pentoxy group, a benzyloxy group, a fluorine atom, a chlorine atom, a bromine atom, an iodine atom or a nitro group;

$R^1$ represents a hydrogen atom, a methyl group, an ethyl group, an n-propyl group, an isopropyl group, an n-butyl group, a sec-butyl group, or a pentyl group;

$R^2$ represents a methyl group, en ethyl group, an n-propyl, an isopropyl group, an n-butyl group, a sec-butyl group, a pentyl group, or a group of Formula (2)

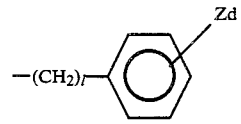

(wherein, Z represents a hydrogen atom, a methyl group, an ethyl group, an n-propyl group, an isopropyl group, an n-butyl group, a sec-butyl group, a pentyl group, a methoxy group, an ethoxy group, an n-propoxy group, an isopropoxy group, an n-butoxy group, a sec-butoxy group, an n-pentoxy group, a fluorine atom, a chlorine atom, a bromine atom or an iodine atom); or $R^1$ and $R^2$ represent, together with the nitrogen atom to which they are attached an azilidino group, a pyrrolidino group, a piperidino group, a hexamethyleneimino group or a morpholino group, 3. The compound of Formula (1) according to claim 2 in which X represents a hydrogen atom, a methyl group, an ethyl group, a chlorine atom, an iodine atom, a hydroxy group, a methoxy group, an ethoxy group, a propoxy group, an isopropoxy group, an n-butoxy group, an isobutoxy group, a sec-butoxy, an n-pentoxy group, an isopentoxy group, a phenoxy group, a chlorophenyl group or a methoxyphenoxy group when a is 1, or a dimethoxy group, a methoxy group and an ethoxy group or a methoxy group and an isopropyl group when a is 2, Y represents a chlorine atom, a bromine atom, a methoxy group, an ethoxy group, a methyl group, a nitro group, a benzyloxy group, or an isopropoxy group when b is 1, or a dimethoxy group when b is 2,

represents a dimethylamino group, a pyrrolidino group, a diethylamino group, a morpholino group, a methylamino group, a cyclopentylamino group, a hexamethyleneimino group,

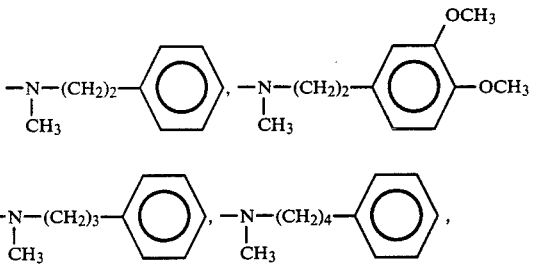

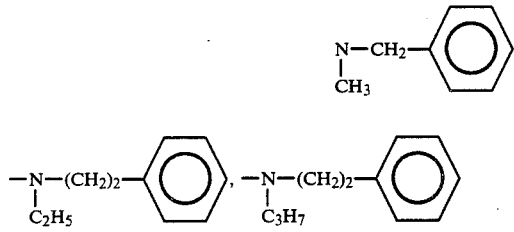

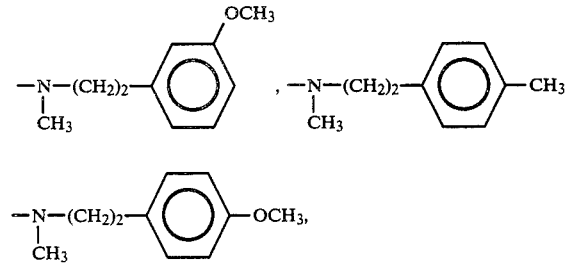

-continued

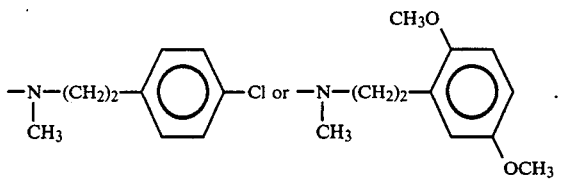

4. The compound of Formula (1) according to claim 3, wherein the compound of Formula (1) is one selected from the group consisting of
2-(2,5-Dimethoxyphenylmethyl)-3-(3-dimethylaminopropyl)-6-isopropoxy-4(3H)-quinazolinone
2-(2,5-Dimethoxyphenylmethyl)-3-(2-pyrrolidinylethyl)-6-methyl-4(3H)-quinazolinone
2-(2,5-Dimethoxyphenylmethyl)-3-(2-dimethylaminoethyl)-6-isopropoxy-4(3H)-quinazolinone
2-(4-Methoxyphenylmethyl)-3-(2-dimethylaminoethyl)-6-isopropoxy-4(3H)-quinazolinone
2-(2,5-Dimethoxyphenylmethyl)-3-2-dimethylaminoethyl)-6-isopropoxy-7-methoxy-4(3H)-quinazolinone
2-(4-Methoxyphenylmethyl)-3-(2-dimethylaminoethyl)-6-isopropoxy-7-methoxy-4(3H)-quinazolinone
2-(2,5-Dimethoxyphenylmethyl)-3-[2-{N-(3,4-dimethoxyphenylethyl)-N-methylamino}-ethyl]-4(3H)-quinazolinone
2-(4-Methoxyphenylmethyl)-3-[2-(N-(3,4-dimethoxyphenylethyl)-N-methylamino}-ethyl]-4(3H)-quinazolinone
2-(4-Methoxyphenylmethyl)-3-[2-{N-(3,4-dimethoxyphenylethyl)-N-methylamino}-ethyl]-6-isopropoxy-4(3H)-quinazolinone and
2-(2,5-Dimethoxyphenylmethyl)-3-[2-{N-(3,4-dimethoxyphenylethyl)-N-methylamino}-ethyl]-6-isopropoxy-4(3H)-quinazolinone.

5. The compound of Formula (1) according to claim 4, wherein said compound is
2-(2,5-Dimethoxyphenylmethyl)-3-(3-dimethylaminopropyl)-6-isopropoxy-4(3H)-quinazolinone.

6. The compound of Formula (1) according to claim 4, wherein said compound is
2-(2,5-Dimethoxyphenylmethyl)-3-(2-pyrrolidinylethyl)-6-methyl-4-(3H)-quinazolinone.

7. The compound of Formula (1) according to claim 4, wherein said compound is
2-(2,5-Dimethoxyphenylmethyl)-3-(2-dimethylaminoethyl)-6-isopropoxy-4(3H)-quinazolinone.

8. The compound of Formula (1) according to claim 4, wherein said compound is
2-(4-Methoxyphenylmethyl)-3-(2-dimethylaminoethyl)-6-isopropoxy-4(3H)-quinazolinone.

9. The compound of Formula (1) according to claim 4, wherein said compound is
2-(2,5-Dimethoxyphenylmethyl)-3-2-dimethylaminoethyl)-6-isoprpoxy-7-methoxy-4(3H)-quinazolinone.

10. The compound of Formula (1) according to claim 4, wherein said compound is
2-(4-Methoxyphenylmethyl)-3-(2-dimethylaminoethyl)-6-isopropoxy-7-methoxy-4(3H)-quinazolinone.

11. The compound of Formula (1) according to claim 4, wherein said compound is
2-(2,5-Dimethoxyphenylmethyl)-3-[2-{N-(3,4-dimethoxyphenylethyl)-N-methylamino}-ethyl]-4(3H)-quinazolinone.

12. The compound of Formula (1) according to claim 4, wherein said compound is
2-(4-Methoxyphenylmethyl)-3-[2-{N-(3,4-dimethoxyphenylethyl) -N-methylamino}-ethyl]-4-(3H)-quinazolinone.

13. The compound of Formula (1) according to claim 4, wherein said compound is
2-(4-Methoxyphenylmethyl)-3-[2-{N-(3,4-dimethoxyphenyethyl) -N-methylamino}-ethyl]-6-isopropoxy-4(3H)-quinazolinone.

14. The compound of Formula (1) according to claim 4, wherein said compound is
2-(2,5-Dimethoxyphenylmethyl)-3-[2-{N-(3,4-dimethoxyphenylethyl) -N-methylamino}-ethyl]-6-isopropoxy-4(3H)-quinazolinone.

15. A composition having calcium antagonism which comprises the compound of Formula (1) in claim 1 or a pharaceutically acceptable acid addition salt thereof as an active ingredient, and a pharmaceutically acceptable carrier.

16. A composition having calcium antagonism which comprises the compound of Formula (1) as defined in claim 2 or a pharmaceutically acceptable acid addition salt thereof as an active ingredient, and a pharmaceutically acceptable carrier.

17. A composition having calcium antagonism which comprises the compound of Formula (1) as defined in claim 3 or a pharmaceutically acceptable acid addition salt thereof as an active ingredient, and a pharmaceutically acceptable carrier.

18. A composition having calcium antagonism which comprises the compound of Formula (1) as defined in claim 4 or a pharmaceutically acceptable acid addition salt thereof as an active ingredient, and a pharmaceutically acceptable carrier.

19. A method of dilating blood vessels or reducing the level of blood pressure based on calcium antagonistic activity, which comprises administering to a human being a pharmaceutically effective amount of the compound of Formula (1) in claim 1.

* * * * *